United States Patent [19]

Douglas et al.

[11] 4,389,285

[45] Jun. 21, 1983

[54] PROCESS INHIBITOR FOR READILY POLYMERIZABLE ETHYLENICALLY UNSATURATED AROMATIC COMPOUNDS

[75] Inventors: Ted L. Douglas; Ambrose J. Clonce, Jr.; Glenn C. Jones, all of Kingsport, Tenn.

[73] Assignee: Eastman Kodak Company, Rochester, N.Y.

[21] Appl. No.: 390,489

[22] Filed: Jun. 21, 1982

[51] Int. Cl.$^3$ ............................ C07C 7/20; B01D 3/34
[52] U.S. Cl. .......................................... 203/9; 203/61; 203/65; 585/5; 585/800; 585/860
[58] Field of Search ........................................ 203/6-9, 203/61, 65; 585/4, 5, 800, 860

[56] References Cited

U.S. PATENT DOCUMENTS

| 2,826,581 | 3/1958 | Mahan et al. | 585/5 |
| 3,407,240 | 10/1968 | Sakashita et al. | 585/5 |
| 3,551,507 | 12/1970 | Sakuragi et al. | 203/9 |
| 3,988,212 | 10/1976 | Watson | 203/9 |
| 4,105,506 | 8/1978 | Watson | 203/9 |
| 4,272,344 | 6/1981 | Watson | 203/9 |

FOREIGN PATENT DOCUMENTS 39-1817  2/1964  Japan .

Primary Examiner—Wilbur L. Bascomb, Jr.
Attorney, Agent, or Firm—David E. Cotey; Daniel B. Reece, III

[57] ABSTRACT

The present invention provides an improvement in methods for preparing and processing ethylenically unsaturated aromatic monomer. The improvement comprises employing 3,5-dinitrosalicylic acid as a process inhibitor. The DNSA is present in a concentration of about 50 to 3000 ppm, preferably about 250 to 2000 ppm, and most preferably about 500 to 1000 ppm.

7 Claims, No Drawings

PROCESS INHIBITOR FOR READILY POLYMERIZABLE ETHYLENICALLY UNSATURATED AROMATIC COMPOUNDS

DESCRIPTION

Background of the Invention

Readily polymerizable ethylenically unsaturated aromatic compounds, such as styrene monomer, are important chemicals of commerce, the current production of styrene monomer being about 10 billion pounds per year. Essentially all of the styrene currently produced is made by processes involving the dehydrogenation of ethylbenzene. Such processes typically include a styrene distillation step wherein the distillation is conducted under a nitrogen atmosphere at a temperature of about 110° C. and a pressure in the range of about 100 to 190 mm Hg. Under these conditions, the reactivity of styrene necessitates the use of a relatively large amount of process inhibitor to prevent polymerization. Likewise, current processes for the production of other ethylenically unsaturated aromatic compounds, such as α-methylstyrene, vinyl toluene, vinyl naphthalene, divinylbenzene, etc., commonly employ vacuum distillation techniques and require the use of a process inhibitor.

The industry currently employs 4,6-dinitro-orthocresol (DNOC) as a process inhibitor. However, DNOC is a highly toxic process inhibitor. The toxicity of DNOC raises exposure concerns with regard to monomer production, the preparation of DNOC stock solutions, and the ill effects of accidental spills. Therefore, there exists a need in the industry for a process inhibitor to replace the highly toxic DNOC.

It has now been found that 3,5-dinitrosalicylic acid (3,5-dinitro-2-hydroxy-benzoic acid; DNSA) can be safely employed as a process inhibitor for readily polymerizable ethylenically unsaturated aromatic compounds. DNSA exhibits an effectiveness equal to or greater than DNOC and has been shown to be much less toxic than DNOC.

Foord et al. disclose in *J. Chem. Soc.*, 1940, pp. 48–56, the effectiveness of quinones as a class of styrene polymerization inhibitors. The reference further discloses the usefulness as polymerization retarders of aromatic compounds having a number of various substituents, including quinonoid, nitro, phenolic hydroxy, amino, and nitroso groups. However, the reference does not disclose the significantly greater inhibitory effect of DNSA over that observed for the other members of the described class of "retarders". Thus, the improved effectiveness of DNSA as a polymerization inhibitor was neither disclosed nor suggested by the prior art. Furthermore, the art did not recognize the toxicity problems posed by certain members of the class of "retarders" and certainly did not propose the use of DNSA as a means for solving those problems.

SUMMARY OF THE INVENTION

The present invention provides an improvement in processes for the preparation of readily polymerizable ethylenically unsaturated aromatic compounds. The improvement comprises employing 3,5-dinitrosalicylic acid as a process inhibitor.

DETAILED DESCRIPTION OF THE INVENTION

The present invention relates to the use of 3,5-dinitrosalicylic acid as a process inhibitor in the preparation of readily polymerizable ethylenically unsaturated aromatic compounds. As used herein, the term "process inhibitor" refers to a polymerization inhibitor which is employed during the preparation and processing of the monomer. Process inhibitors can be distinguished from product inhibitors, which are combined with the monomer in order to inhibit polymerization during storage and handling.

According to the process of the present invention, 3,5-dinitrosalicylic acid (DNSA) is employed as a process inhibitor during the preparation and processing of certain monomeric substances. DNSA is a well-known chemical compound whose preparation is also well known in the art. DNSA is available commercially from a number of sources.

The present process is applicable to readily polymerizable ethylenically unsaturated aromatic compounds. Such compounds include styrene, α-methylstyrene, vinyl toluene, vinyl naphthalene, divinylbenzene, etc. Compounds preferred for use in the process of the present invention include styrene and α-methylstyrene, with styrene being particularly preferred. While portions of the present specification refer specifically to styrene as an illustrative member of this class of compounds, it is to be understood that this specification applies to all members of the described class of readily polymerizable ethylenically unsaturated aromatic compounds.

As stated above, during the latter stages of current processes for the production of ethylenically unsaturated aromatic compounds, the crude monomer is typically subjected to vacuum distillation in order to remove excess reactants and other volatile aromatic impurities. In accordance with the process of the present invention, DNSA is employed as a process inhibitor during the preparation of the monomer and especially during the distillation step, which is when polymerization is most likely to occur.

The DNSA can be supplied to the process in a variety of ways. It can be introduced at the beginning of the reaction, for example, a dehydrogenation reaction in the case of certain of the compounds (such as styrene), and be present in the reaction stream from the initiation of the reaction through the distillation of the crude monomer. Alternatively, the DNSA can be provided to the vessel in which the distillation of the crude monomer occurs. In preferred embodiments, the major portion of the DNSA is provided to the reaction system at the beginning of the reaction for the production of monomer, and an additional minor amount of DNSA is fed near the top of the apparatus for the distillation of the crude monomer and is allowed to fall through the distillation apparatus in a direction countercurrent to the direction of flow of the impurities being distilled from the crude monomer. Such impurities often include the initial reactant, such as ethylbenzene in the case of the production of styrene. Thus, in such a preferred scheme, the total amount of DNSA process inhibitor present in the system is available for intimate contact with the monomer in the distilland. Regardless of the manner in which the DNSA is provided to the reaction system, the DNSA is typically removed from the system in the final distillation whereby crude monomer is taken overhead and the remaining impurities and the DNSA inhibitor are taken off as bottoms from the column.

The DNSA is provided to the reaction system in an amount which is sufficient to effect the inhibition of polymerization. Typically, the DNSA will be present in an amount of about 50 to 3000 ppm, based upon the weight of DNSA per total weight of reactants and products present in the distilland. Preferably, the DNSA is present in a concentration of about 250 to 2000 ppm, with a concentration of about 500 to 1000 ppm being especially preferred.

DNSA can be provided to the styrene preparation process either directly or as a stock solution. DNSA is sufficiently soluble in suitable carrier solvents to allow the preparation of such a stock solution. Suitable carrier solvents include alpha-methylbenzyl alcohol, mixtures of alpha-methylbenzyl alcohol and acetophenone (e.g., a 15:85 acetophenone:alpha-methylbenzyl alcohol blend), etc. The use of stock solutions of process inhibitors is well known in the art and is a wide-spread practice.

Additional inhibitors may also be present during the process of the present invention. For example, product inhibitors, such as t-butylcatechol, may also be present during the preparation and/or distillation of the crude monomer.

The invention will be further illustrated by the following Examples although it will be understood that these Examples are included merely for purposes of illustration and are not intended to limit the scope of the invention.

EXAMPLE 1

This Example illustrates the improved inhibiting effect provided by DNSA.

In each run of the present Example, the indicated amount of DNSA was added to 500 ml of commercial styrene monomer containing 50 ppm t-butylcatechol (TBC). The inhibited sytrene was refluxed under sufficient vacuum to maintain the temperature at 100° C. After three hours of reflux and after six hours of reflux, 10-gram samples were contacted with 15 ml of methyl alcohol, causing any polymer present in the sample to precipitate. The polymer was collected, dried at 210° C., and weighed. The results are listed in Table I.

TABLE I

| DNSA Concentration | Percent Polymer Formation | |
|---|---|---|
| (ppm) | 3 Hrs. Reflux | 6 Hrs. Reflux |
| 250 | 0.90 | 5.9 |
| 500 | 0.30 | 1.5 |
| 1000 | 0.10 | 0.3 |
| 1500 | 0.04 | 0.12 |
| 2000 | 0.00 | 0.06 |

COMPARATIVE EXAMPLE 1

Example 1 was repeated except that the DNSA was replaced with 4,6-dinitro-ortho-cresol (DNOC) which was obtained commercially from Blue Spruce International. The results are given in Table II.

TABLE II

| DNOC Concentration | Percent Polymer Formation | |
|---|---|---|
| (ppm) | 3 Hrs. Reflux | 6 Hrs. Reflux |
| 250 | 1.9 | 8.3 |
| 500 | 0.75 | 2.2 |
| 1000 | 0.30 | 0.90 |
| 1500 | 0.14 | 0.24 |
| 2000 | 0.07 | 0.04 |

It can be seen from a comparison of the data of Tables I and II that DNSA is far more effective as a process inhibitor than is DNOC. In virtually every case, the percent polymer formation for DNSA is approximately half or less than that for DNOC. In addition, DNSA is much less toxic than DNOC. Therefore, its use as a process inhibitor is far more safe and effective than is the use of DNOC.

EXAMPLE 2

Example 1 was repeated except that 500 ppm DNSA was added to distilled styrene and to distilled styrene to which 50 ppm t-butylcatechol had been added. The results are given in Table III.

TABLE III

| Monomer | Percent Polymer Formation | |
|---|---|---|
| | 3 Hrs. Reflux | 6 Hrs. Reflux |
| distilled styrene | 0.06 | 0.72 |
| distilled styrene + 50 ppm TBC | 0.09 | 0.80 |

COMPARATIVE EXAMPLE 2

Example 2 was repeated except that the DNSA was replaced with DNOC. The results are given in Table IV.

TABLE IV

| Monomer | Percent Polymer Formation | |
|---|---|---|
| | 3 Hrs. Reflux | 6 Hrs. Reflux |
| distilled styrene | 0.39 | 1.7 |
| distilled styrene + 50 ppm TBC | 0.28 | 1.7 |

Again, Tables III and IV demonstrate the improved effectiveness of DNSA as a styrene process inhibitor both in the presence and absence of TBC as product inhibitor.

The invention has been described in detail with particular reference to preferred embodiments thereof, but it will be understood that variations and modifications can be effected within the spirit and scope of the invention.

We claim:

1. In processes for the preparation of readily polymerizable ethylenically unsaturated aromatic compounds, the improvement which comprises employing 3,5-dinitrosalicylic acid as a process inhibitor.

2. The process of claim 1 wherein said 3,5-dinitrosalicylic acid is present in a concentration of about 50 to 3000 ppm.

3. The process of claim 1 wherein said 3,5-dinitrosalicylic acid is present in a concentration of about 250 to 2000 ppm.

4. The process of claim 1 wherein said readily polymerizable ethylenically unsaturated aromatic compound is selected from styrene, α-methylstyrene, vinyl toluene, vinyl naphthalene, divinylbenzene, and mixtures thereof.

5. The process of claim 4 wherein said readily polymerizable ethylenically unsaturated aromatic compound comprises styrene.

6. In a process for the preparation of styrene which includes a distillation step at elevated temperature and/or reduced pressure, the improvement which comprises providing 3,5-dinitrosalicylic acid to the distilland in a concentration of about 250 to 2000 ppm.

7. The process of claim 6 wherein said 3,5-dinitrosalicylic acid is present in the distilland in a concentration of about 500 to 1000 ppm.

* * * * *